US008491456B2

(12) United States Patent
Park et al.

(10) Patent No.: US 8,491,456 B2
(45) Date of Patent: Jul. 23, 2013

(54) METHOD AND APPARATUS PROVIDING A SYMBOL SEQUENCE TO A USER, AND WEARABLE INFRASTRUCTURE PROVIDING THE SYMBOL SEQUENCE TO THE BODY

(76) Inventors: Song Park, Berkeley, CA (US); Earle W. Jennings, Kensington, CA (US)

( * ) Notice: Subject to any disclaimer, the term of this patent is extended or adjusted under 35 U.S.C. 154(b) by 1288 days.

(21) Appl. No.: 11/213,126

(22) Filed: Aug. 26, 2005

(65) Prior Publication Data

US 2006/0047231 A1 Mar. 2, 2006

Related U.S. Application Data

(60) Provisional application No. 60/605,278, filed on Aug. 26, 2004.

(51) Int. Cl.
*A61M 21/00* (2006.01)

(52) U.S. Cl.
USPC .......... 600/28

(58) Field of Classification Search
USPC .......... 600/9–15, 26–28; 607/1–3, 45–48, 607/50, 55–60, 62, 63, 66–69, 72, 74–76, 607/88, 115, 136, 145, 148–152, 154, 156, 607/900; 606/41, 42, 189, 237, 204; 381/2, 381/23.1, 71.1, 73.1, 74, 150, 182, 300, 301, 381/306, 309–312, 322, 370–374, 376–383, 381/385; 331/78; 128/897–898, 902, 907; 181/126, 128–129; 601/15–22, 47–67
See application file for complete search history.

(56) References Cited

U.S. PATENT DOCUMENTS

| | | | | | |
|---|---|---|---|---|---|
| 4,170,275 | A | * | 10/1979 | Larsen | 181/129 |
| 4,500,019 | A | * | 2/1985 | Curley, Jr. | 224/222 |
| 4,864,619 | A | * | 9/1989 | Spates | 381/309 |
| 4,895,149 | A | * | 1/1990 | Morez | 607/2 |
| 5,417,706 | A | * | 5/1995 | Chun | 606/189 |
| 5,966,164 | A | * | 10/1999 | Gotoh et al. | 348/14.01 |
| 6,267,721 | B1 | * | 7/2001 | Welles | 600/26 |
| 6,355,006 | B1 | * | 3/2002 | Ryaby et al. | 601/2 |
| 6,393,319 | B1 | * | 5/2002 | Bock et al. | 607/2 |
| 6,843,765 | B2 | * | 1/2005 | Kawamata | 600/28 |
| 6,939,324 | B2 | * | 9/2005 | Gonnelli et al. | 604/142 |
| 7,097,610 | B2 | * | 8/2006 | Woo | 600/15 |
| 7,229,423 | B2 | * | 6/2007 | Horzewski et al. | 601/21 |
| 2002/0039424 | A1 | * | 4/2002 | Watanuki | 381/74 |
| 2002/0173968 | A1 | * | 11/2002 | Parry | 704/500 |
| 2003/0182003 | A1 | * | 9/2003 | Takashima | 700/94 |
| 2003/0199792 | A1 | * | 10/2003 | Austin | 601/1 |
| 2003/0200002 | A1 | * | 10/2003 | Kwon | 700/94 |
| 2004/0044384 | A1 | * | 3/2004 | Leber et al. | 607/88 |
| 2004/0141624 | A1 | * | 7/2004 | Davis et al. | 381/73.1 |

* cited by examiner

*Primary Examiner* — Christine Matthews
*Assistant Examiner* — Catherine E Burk
(74) *Attorney, Agent, or Firm* — Earle Jennings

(57) ABSTRACT

A wearable infrastructure is used with a music/multimedia player to acoustically provide at last one symbol sequence to at least one biologically active zone on the user wearing the wearable infrastructure. The invention includes the symbol coding sequence as a program system comprising program steps residing in a memory accessibly coupled to a computer within the music/multimedia player, directing the music/multimedia player to deliver the symbol sequence to at least one of the possibly multiple transponders. The program steps are often coded in an intermediate language interpreted by the computer.

21 Claims, 13 Drawing Sheets

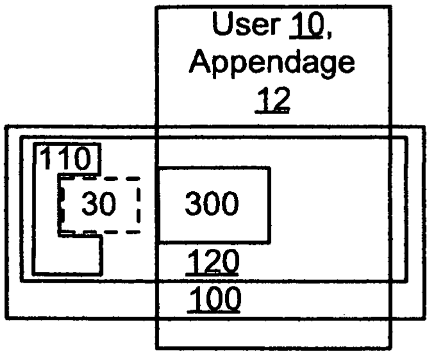
Fig. 1A
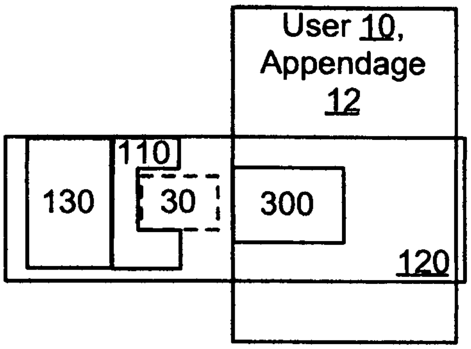
Fig. 1B
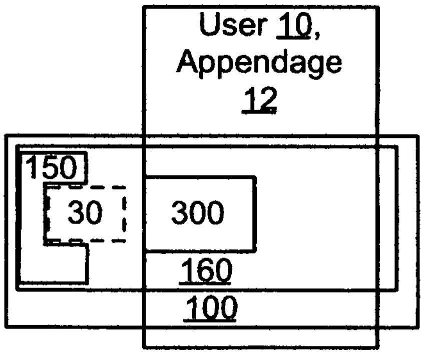
Fig. 1C
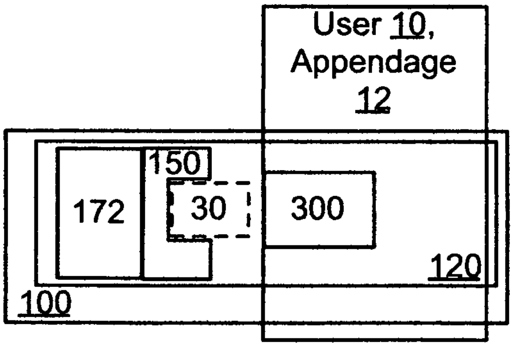
Fig. 1D
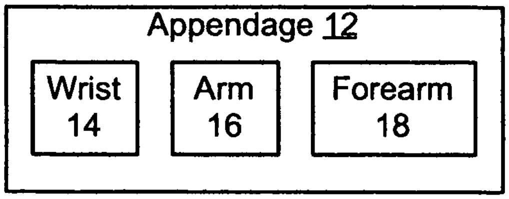
Fig. 1E
Fig. 1F
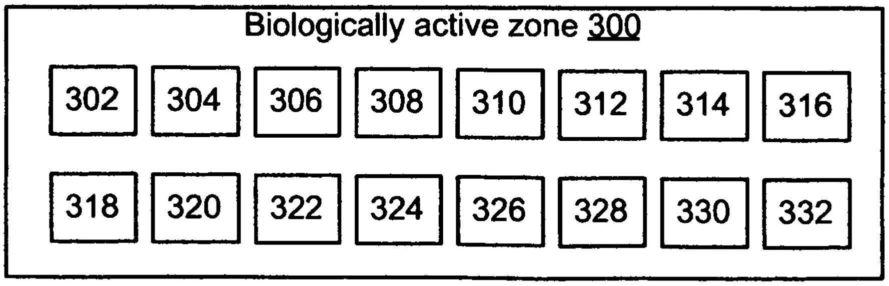

Fig. 12C

| Vowels Chinese Elements | Consonants + Vowel ‘A’ (Tibetan Elements) | | | | | | |
|---|---|---|---|---|---|---|---|
| O Origin<br>OH<br>IO | Earth<br>Solid body parts | Water<br>Liquid body parts | Fire<br>Metabolism | Air<br>Circulation & movement | Space<br>Structure | Superficial<br>Deep-aspirated<br>Soft | Organ |
| E Wood<br>EH<br>IE | CHA<br>CH’A<br>CHIA | SHA<br>SH’A<br>SHIA | JA<br>J’A<br>JIA | JHA<br>JH’A<br>JHIA | YA<br>Y’A<br>YIA | Superficial<br>Deep-aspirated<br>Soft | Liver Tendons Spleen |
| A Fire<br>AH<br>IA | KA<br>K’A<br>KIA | HA<br>H’A<br>HIA | GA<br>G’A<br>GIA | GHA<br>GH’A<br>GHIA | NGA<br>NG’A<br>NGIA | Superficial<br>Deep-aspirated<br>Soft | Vessels Heart & S mall intestine |
| EU Earth<br>EUH<br>IEU | TRA<br>TR’A<br>TRYA | RZHA<br>RZH’A<br>RZHYA | RRA<br>RR’A<br>RRIA | RA<br>R’A<br>RIA | LA<br>L’A<br>LIA | Superficial<br>Deep-aspirated<br>Soft | Muscle Spleen & Stomach |
| I Metal<br>IH<br>II | TA<br>T’A<br>TIA | SA<br>S’A<br>SIA | DA<br>D’A<br>DIA | ZA<br>Z’A<br>ZIA | NA<br>N’A<br>NIA | Superficial<br>Deep-aspirated<br>Soft | Skin Lungs & L arge Intestine |
| U Water<br>UH<br>IU | PA<br>P’A<br>PIA | FA<br>F’A<br>FIA | BA<br>B’A<br>BYA | WA<br>W’A<br>WIA | MA<br>M’A<br>MIA | Superficial<br>Deep-aspirated<br>Soft | Bone, Bladder, Urinary, Kidney |
| | Spleen & Stomach | Kidney & Bladder | Liver & Gall bladder | Lungs & Large Intestines | Heart & Small Intestines | | |

METHOD AND APPARATUS PROVIDING A SYMBOL SEQUENCE TO A USER, AND WEARABLE INFRASTRUCTURE PROVIDING THE SYMBOL SEQUENCE TO THE BODY

CROSS-REFERENCE TO RELATED APPLICATIONS

This application claims priority to provisional application No. 60/605,278 filed Aug. 26, 2004, which is incorporated herein by reference.

TECHNICAL FIELD

This invention relates to wearable infrastructures acoustically providing at least one symbol sequence to at least one biologically active zone of the body, and to the symbol coding sequences as program systems directing computers in music/multimedia players to deliver the symbol sequences to transponders kept by the wearable infrastructures.

BACKGROUND OF THE INVENTION

Contemporary life tends to be hectic, alienating, and often leaving many people without a sense of support in the natural processes of exercise, rest and recuperation. Many, if not most, of us, do not have access to gymnasiums, massages, acupuncture, and other exemplary systems and activities that improve our lives through exercise, rest and recuperation. Even those who do have access, often face substantial expense in using these capabilities. People need inexpensive avenues supporting and/or augmenting exercise, rest and recuperation.

In the United States, there is a large population of people who were born in the late 1940's through the early 1960's. These people were nicknamed the "baby boomers", or now as they age, the "boomers". In 2005, their oldest are turning 60, and in five years, they turn 65. For seven decades, society provided substantial medical and social aid at that age. The projections are that the boomers will bankrupt the medical and social aid infrastructure by around 2015. Aging individuals will need inexpensive techniques and mechanisms to support or improve their health outside the existing medical infrastructure, if they are to receive aid and the society of this country is to have any chance of averting a medical, fiscal, and humanitarian crisis.

Today, there are literally millions, if not tens of millions, of lightweight, wearable music/multimedia players being used by people every day. All these players support at least one audio output channel, and quite often two audio channels. Most of these players are capable of delivering enough volume to head phones that the music they play can be heard over the noise of trains, traffic, and the like. Their main benefit to people is that they permit individuals some control over what they hear. These devices have not been harnessed to improve people's health.

SUMMARY OF THE INVENTION

The inventors believe the invention offers a substantial opportunity to at least partly avert the medical, fiscal and humanitarian crisis related to the aging baby boom, by using existing music/multimedia players with a wearable infrastructure to acoustically provide at last one symbol sequence to at least one biologically active zone on the user wearing the wearable infrastructure. Consequently, the invention will focus on a few of the preferred embodiments disclosed in the above cited provisional application. Many of the other embodiments are useful and important, and will be developed in subsequent applications.

The invention includes the symbol coding sequence as a program system comprising program steps residing in a memory accessibly coupled to a computer within the music/multimedia player, directing the music/multimedia player to deliver the symbol sequence to at least one of the possibly multiple transponders. The program steps are often coded in an intermediate language interpreted by the computer. Typical implementations of the intermediate language include the MPEG 1 Layer 3 audio coding scheme, often known as MP3, versions of the Windows Media File format, versions of MPEG 4, and so on, to cite some examples.

The inventors have repeatedly found that the providing of symbol sequences acoustically to biologically active zones improves various conditions associated with their bodies and the bodies of several others. They have experimented with a music player using a prototype wearable infrastructure and a symbol sequence to aid a weak organ in the other inventor, which has proven beneficial to that individual. While these experiences and experiments were not setup or recorded to provide medical proofs of the effectiveness of the invention, they do constitute an actual reduction to practice of the invention. Those reading this document are reminded that by law, these statements by the inventors are an affidavit submitted to the United State Patent and Trademark Office regarding the patentability of the invention.

The delivery of the symbol sequence to the at least one transponder may include at least one wire line physical transport and/or at least one wireless physical transport. The wire line physical transport may use commonly available headphones coupled by wires to a headphone jack, with the headphones acting as the transponders. Alternatively, the transponder(s) may couple with the music/multimedia player through a wireless physical transport, which may support a version of a wireless communications protocol. By way of example, the wireless communications protocol may implement a version of the Bluetooth communications protocol standard.

The wearable infrastructure couples with at least one transponder to provide at least one symbol sequence to the at least one biologically active zone, where the wearable infrastructure keeps the transponder near the biologically active zone on a user wearing the wearable infrastructure. The transponder provides the symbol sequence to the biologically active zone through an acoustic carrier medium as sound to the user, who is a human being.

The symbol sequence includes a succession of at least two, and preferably at least three symbols. This provides the signal, which is modulated for the carrier medium and provided at the biologically active zone. The symbols are formed of the spoken letters of Song Park's meta-alphabet as disclosed on and incorporated herein from pages 12 and 13 of the provisional application No. 60/605,278 filed Aug. 26, 2004 as FIG. 12C. As stated in the provisional application, the alphabet includes all combinations of consonants followed by vowels and vowels followed by consonants. The same combination of vowel+consonant has a different effect that consonant+vowel. Each alphabet syllable has two articulations, inhaling and exhaling, which have different effects. When syllable starts with consonant, it releases corresponding elemental energy and directs it depending on the vowel, creating a particular action. KA activates, directing energy upward. KU passives, directs energy downward, absorbs. When syllable starts with vowel, the energy is lead toward the organ or system. KA releases energy form organ, AK leads toward organ. The inventor's research indicates that this alphabet is a strict superset of Russian, Korean, Sanscrit, Tibetan, Japanese, the major languages of China, French, Spanish, Italian, German, Greek, English, Farsi, Hebrew, Arabic, Navaho.

The wearable infrastructure preferably includes at least one of the following wearable infrastructure components: a wrist harness similar to a bracelet or wrist band, a forearm harness similar to a forearm wrap or binding, and an arm harness similar to an arm band.

In general, the biologically active zone includes at least one of the following. At least one point and/or meridian as defined in acupuncture, acupressure and/or shiatsu. The minimal scope of these meridians are defined in Chapter Four, "The Meridians: . . . " pages 77 to 114, in *The Web That Has No Weaver: Understanding Chinese Medicine*, by Ted Kaptchuk © 1983, ISBN 0-8092-2933-1. A reflexology correspondence point. A pressure point as used in Karate, Tai Chi and Tai Kwan Do. The regions and points named and used in Tibetan medicine, as shown in *Tibetan Medical Paintings: Illustrations to the Blue Beryl treatise of Sangye Gyamtso* (1653-1705), © 1992 Serinda Publications, ISBN 0-8109-3861-8, two volumes. The regions and points named and used in Western Medicine, including but not limited to the named points and regions of the respiratory, muscular, arterial, fascial, and nervous system as shown in *Gray's Anatomy.*

The wearable infrastructure may be the wrist harness, which may preferably stimulate the lung meridian. The wrist harness may further preferably stimulate the lung and heart meridian. It may further preferably stimulate the pericardium and triple warmer meridians. The triple warmer meridian is also known as the triple burner meridian.

The method of operating the invention includes the following steps. Keeping at least one transponder near at least one biologically active zone of a user wearing the transponder. Using the transponder to provide the symbol sequence to the biologically active zone of the user to alter the user. Keeping the transponder near the biologically active zone may further include keeping the transponder touching the biologically active zone at least some of the time, and in certain embodiments, all the time the invention is operating.

Using the transponder may include using it to provide the symbol sequence to more than one biologically active zone.

Using the transponder may include using it to provide the symbol sequence within a given time period. The time period may be repeated and/or vary over time.

Keeping at least one transponder near at least one biologically active zone may include keeping more than one of the transponders near more than one of the biologically active zones. While in this application, there is a preference for the carrier medium to be acoustic, in certain embodiments, there may be more than one preferred carrier medium. The biologically active zones may or may not all be from the same medical system. By way of example, acupuncture point and trigger points may be used for the biologically active zones.

BRIEF DESCRIPTION OF THE DRAWINGS

FIGS. 1A to 1D show aspect of the invention's wearable harness;

FIG. 1E shows aspects of the appendage of the user of FIGS. 1A to 1D;

FIG. 1F show examples of the biologically active zone of FIGS. 1A to 1D;

FIGS. 4A to 5A show some aspects of the operation and apparatus of the wearable infrastructure;

FIGS. 6A to 7A show details of the distribution device of FIG. 5A;

DETAILED DESCRIPTION

Figure 2A:
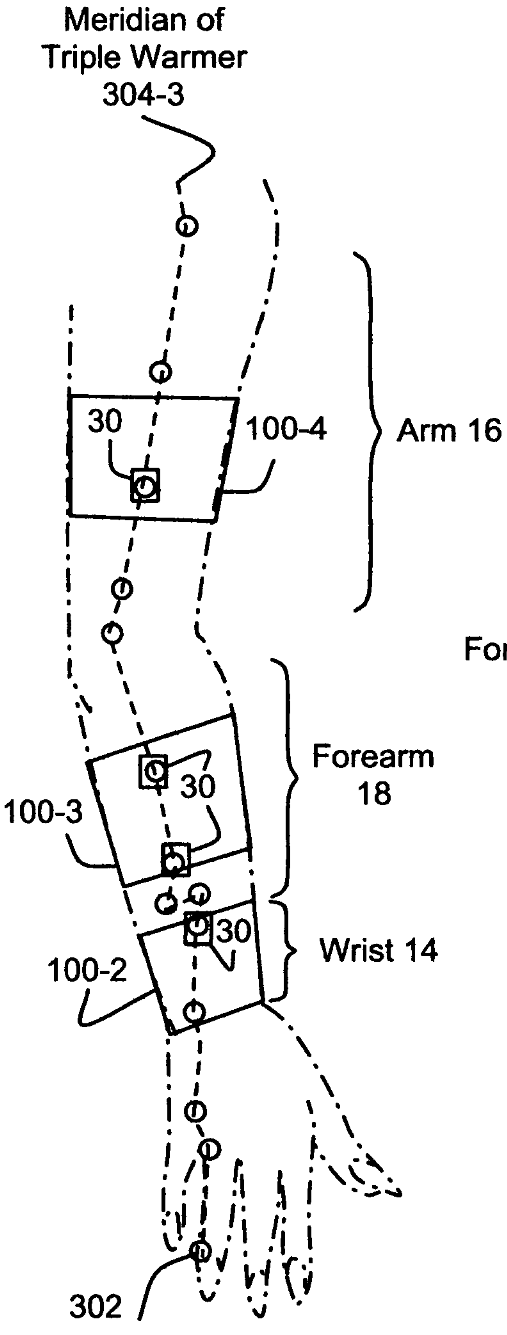
FIGS. 2A to 3B show examples of the wearable harness for various appendages keeping transponders near various biologically active zones.

This invention relates to wearable infrastructures acoustically providing at least one symbol sequence to at least one biologically active zone of the body, and to the symbol coding sequences as program systems directing computers in music/multimedia players to deliver symbol sequences to transponders kept by the wearable infrastructures.

The inventors believe the invention offers a substantial opportunity to at least partly avert the medical, fiscal and humanitarian crisis related to the aging baby boom. The invention uses an existing music/multimedia player 20 with the invention's wearable infrastructure 100 to acoustically provide 36 at last one symbol sequence 200 to at least one biologically active zone 300 on the user 10 wearing the wearable infrastructure, as shown in FIGS. 1A to 1D, 2A to 5A, and 6A. Consequently, the invention will focus on a few of the preferred embodiments disclosed in the above cited provisional application. Many of the other embodiments are useful and important, and will be developed in subsequent applications.

Figure 4A:
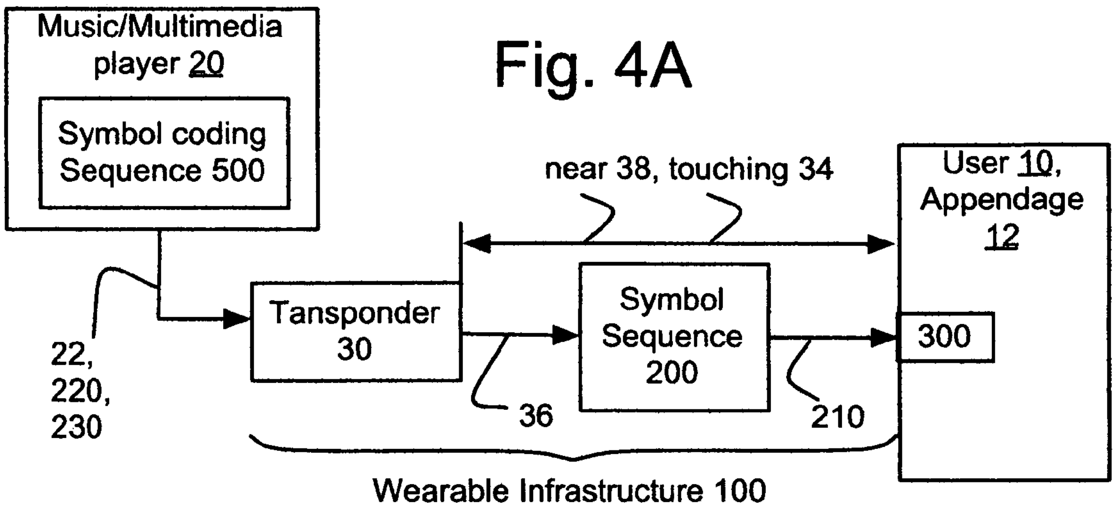
Figure 8A:
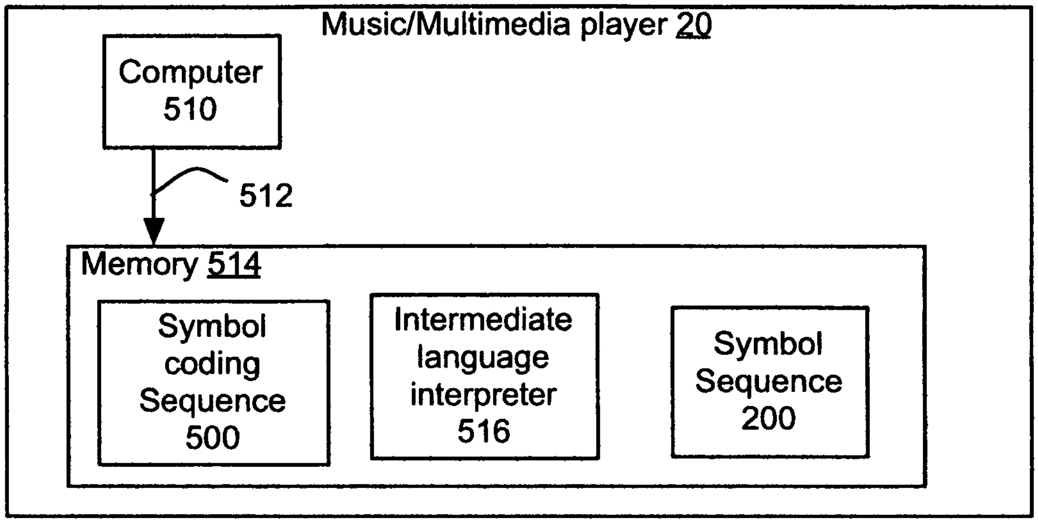
FIGS. 8A, 8B and 9B show some aspects of the symbol coding sequence of FIG. 4A.
Figure 8B:
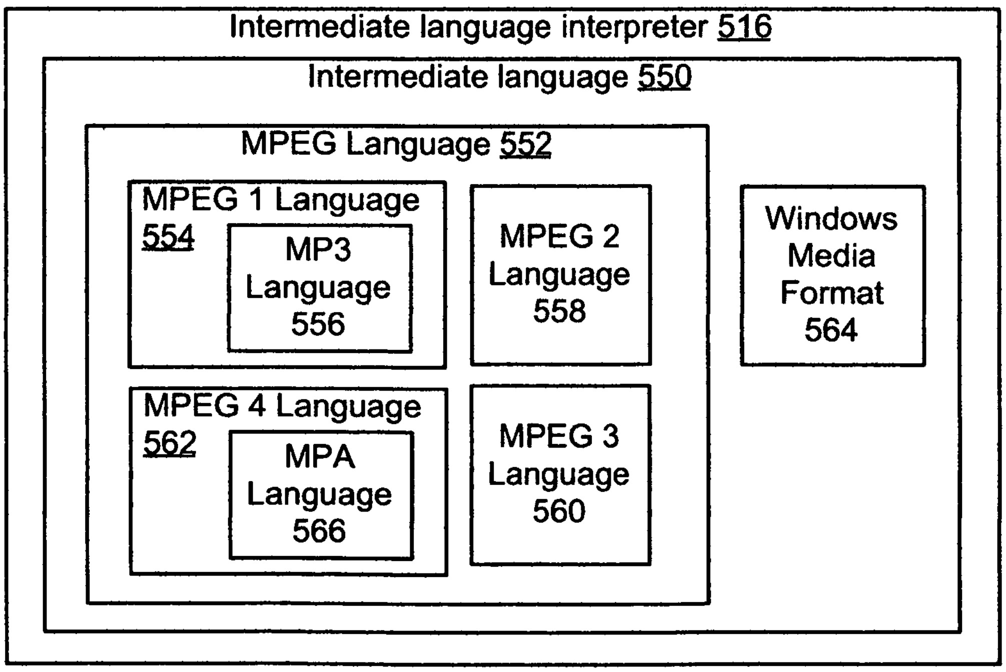

The invention includes the symbol coding sequence 500 as a program system 520 comprising program steps residing in a memory 514 accessibly coupled 512 to a computer 510 within the music/multimedia player 20, as shown in FIGS. 4A and 8A. The symbol coding system directs the music/multimedia player to deliver 22 the symbol sequence to at least one transponder 30. The program steps are often coded in an intermediate language 550 interpreted by the computer, often using specialized software known herein as an intermediate language interpreter 516, as further shown in FIG. 8B.

By way of example, the intermediate language 550 may include a Motion Picture Experts Group, or MPEG Language 552. Today, it is common to think of MPEG languages as include a MPEG 1 language 554, a MPEG 2 language 558, a MPEG 3 language 560, and a MPEG 4 language 562. A commonly available intermediate language is the MP3 language 556, which is part of the MPEG 1 Language. The MPA language 566, which is part of the MPEG 4 Language is commonly supported by the music/multimedia player 20 family made by the Apple Corporation. Typical implementations of the intermediate language may also include a version of the Windows Media File format 564, and so on.

The inventors have repeatedly found that acoustically providing 36 a symbol sequence 200 to biologically active zones improves various conditions associated with their bodies and the bodies of another. They have experimented with a music/ multimedia player 20 using a prototype wearable infrastructure 100 and a symbol sequence 200 to aid weak organs in the one of the inventors, which has proven beneficial to that individual. While these experiences and experiments were not setup or recorded to provide medical proofs of the effectiveness of the invention, they do constitute an actual reduction to practice of the invention. Those reading this document are reminded that by law, these statements by the inventors are an affidavit submitted to the United State Patent and Trademark Office regarding the patentability of the invention.

The delivery of the symbol sequence to the at least one transponder may include at least one wire line physical transport and/or at least one wireless physical transport.

Figure 4B:
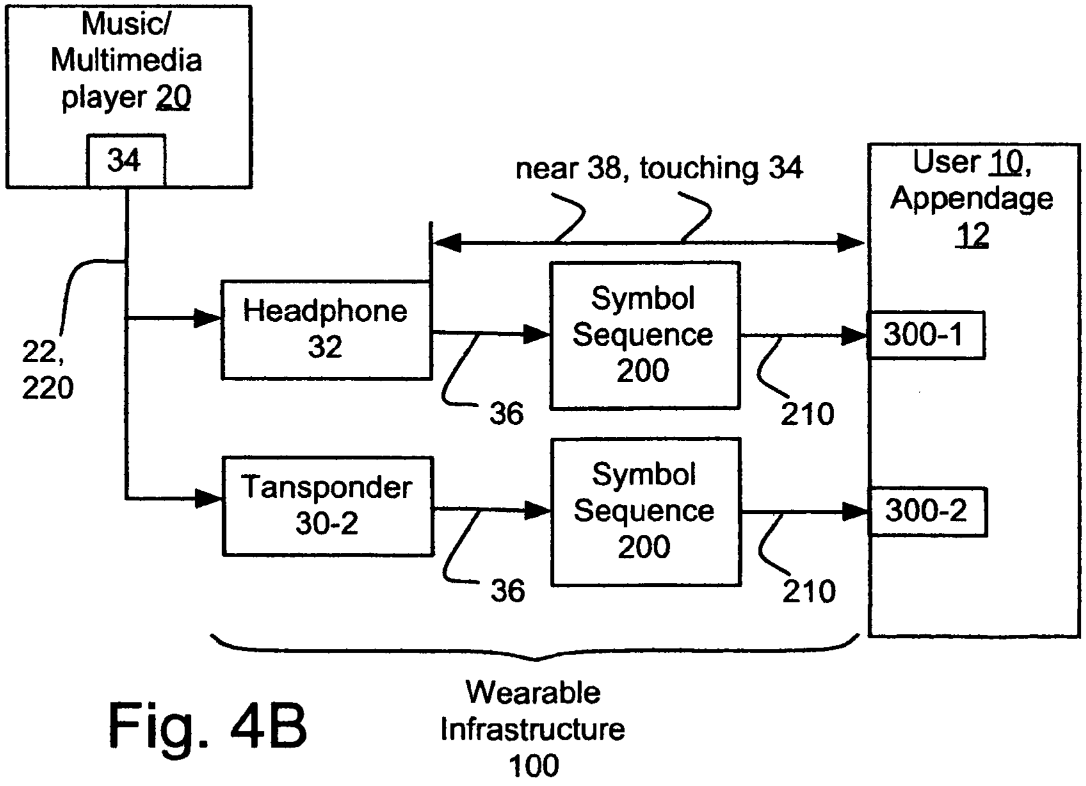
Figure 9A:
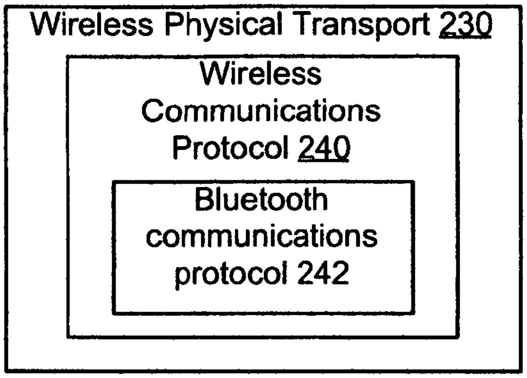
FIG. 9A shows some aspects of the wireless physical transport of FIG. 4A.
Figure 9B:
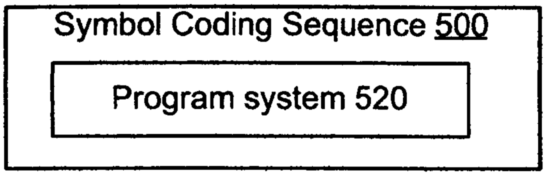

The delivery 22 of the symbol sequence 200 to the at least one transponder 30 may include at least one wire line physical transport 220, as in FIGS. 4A and 4B, and/or at least one wireless physical transport 230, as in FIG. 4A. The wire line physical transport may use at least one commonly available headphone 32 coupled by wires to a headphone jack 34, with the headphone acting as the transponder 30. Alternatively, the transponder(s) may couple with the music/multimedia player through a wireless physical transport, which may support a version of a wireless communications protocol 240, as shown in FIG. 9A. By way of example, the wireless communications protocol may implement a version of the Bluetooth communications protocol 242 standard.

Returning to the overall operation of the invention, as shown in FIGS. 4A to 5A. The wearable infrastructure 100 couples with at least one transponder 30 to provide at least one symbol sequence 200 to the at least one biologically active zone 300, where the wearable infrastructure keeps the transponder near 38 the biologically active zone on a user 10 wearing the wearable infrastructure. The transponder 30 provides 36 the symbol sequence to the biologically active zone through an acoustic carrier medium 210 as sound to the user, who is a human being.

Figure 5A:
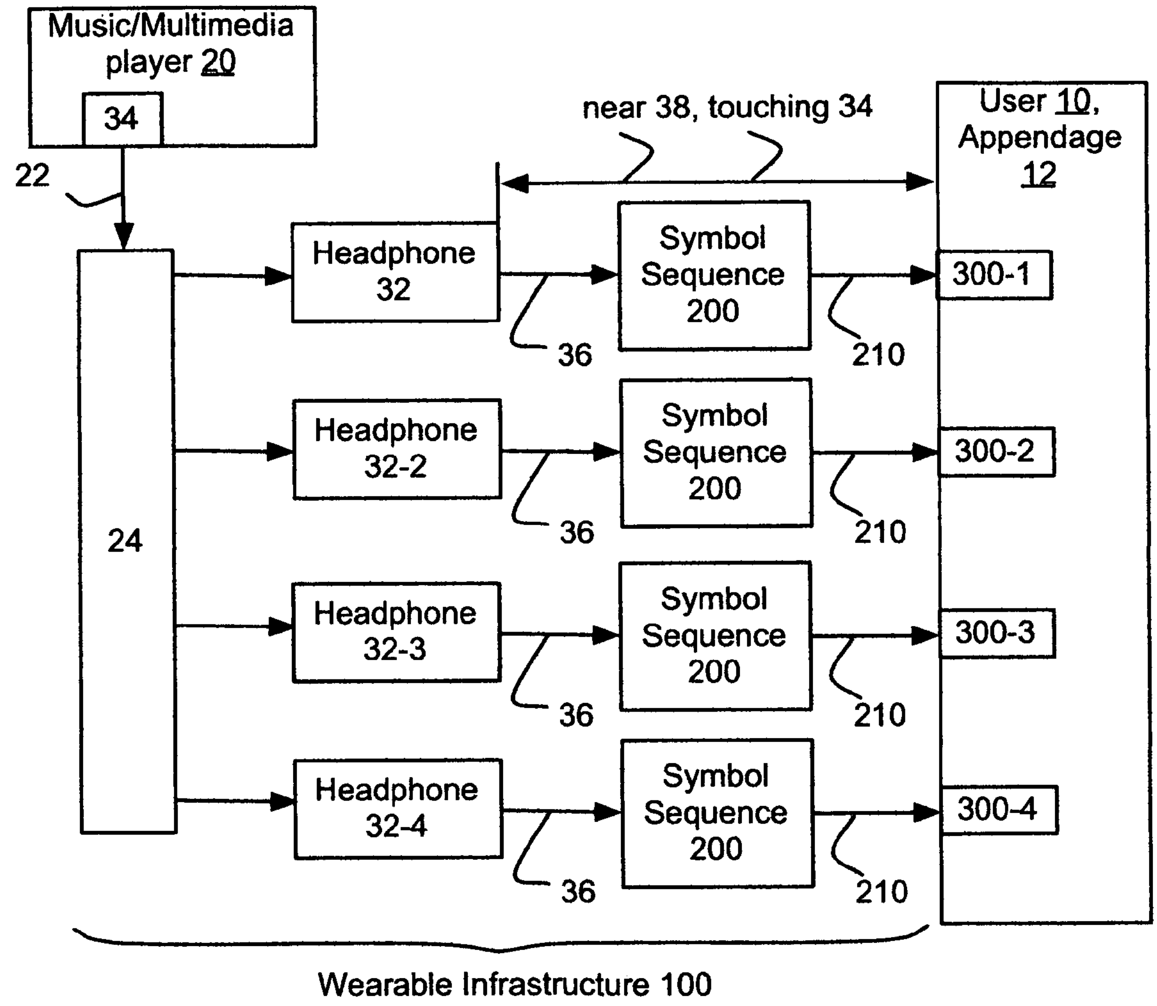
Figure 5B:
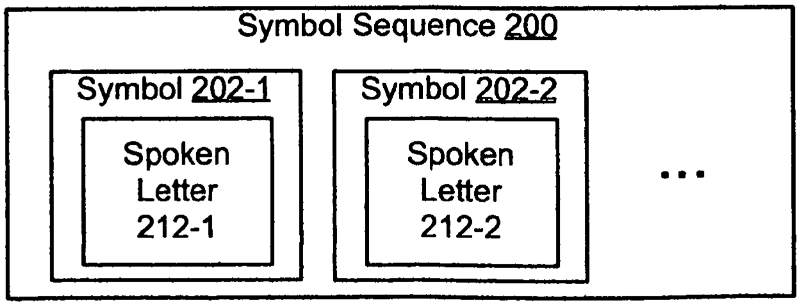
FIG. 5B shows an example of the symbol sequence of FIGS. 4A to 5A.

The symbol sequence includes a succession of at least two, and preferably at least three symbols, as shown in FIG. 5B. The symbols are formed of the spoken letters of Song Park's meta-alphabet. The symbol sequence 200 includes a symbol 202, which is a spoken letter 212 of the meta-alphabet 210. The symbol sequence further includes a second symbol, which is a second spoken letter 212-2 of the meta-alphabet. The symbol sequence provides a signal, which is modulated for the carrier medium and acoustically provided 36 at the biologically active zone 300.

The wearable infrastructure 100 preferably includes at least one of the following wearable infrastructure components: a wrist harness 100-2 similar to a bracelet or wrist band, a forearm harness 100-3 similar to a forearm wrap or binding, and an arm harness 100-5 similar to an arm band, as shown in FIGS. 2A to 2D. in certain embodiments, the wearable infrastructure is the wrist harness.

In general, the biologically active zone 300 includes at least one of the following, as shown in FIG. 1F. At least one point of a meridian 302 and/or meridian 304 as defined in acupuncture, acupressure and/or shiatsu. The minimal scope of these meridians are defined in Chapter Four, "The Meridians: . . . " pages 77 to 114, in *The Web That Has No Weaver: Understanding Chinese Medicine*, by Ted Kaptchuk © 1983, ISBN 0-8092-2933-1. A reflexology correspondence point 306. A pressure point 308 as used in Karate, Tai Chi and Tai Kwan Do. A region in Tibetan medicine 310 and a point in Tibetan medicine 312, as shown in *Tibetan Medical Paintings: Illustrations to the Blue Beryl treatise of Sangye Gyamtso* (1653-1705), © 1992 Serinda Publications, ISBN 0-8109-3861-8, two volumes. The regions and points named and used in Western Medicine, including but not limited to the named points and regions of the respiratory, muscular, arterial, fascial, and nervous system as shown in *Gray's Anatomy*.

Among these are the respiratory system region 316, the respiratory system point 314, the muscular system region 320, the muscular system point 318, the arterial system region 324, the arterial system point 322, the fascial system region 328, the fascial system point 326, the nervous system region 332, and the nervous system point 330.

Figure 2B:
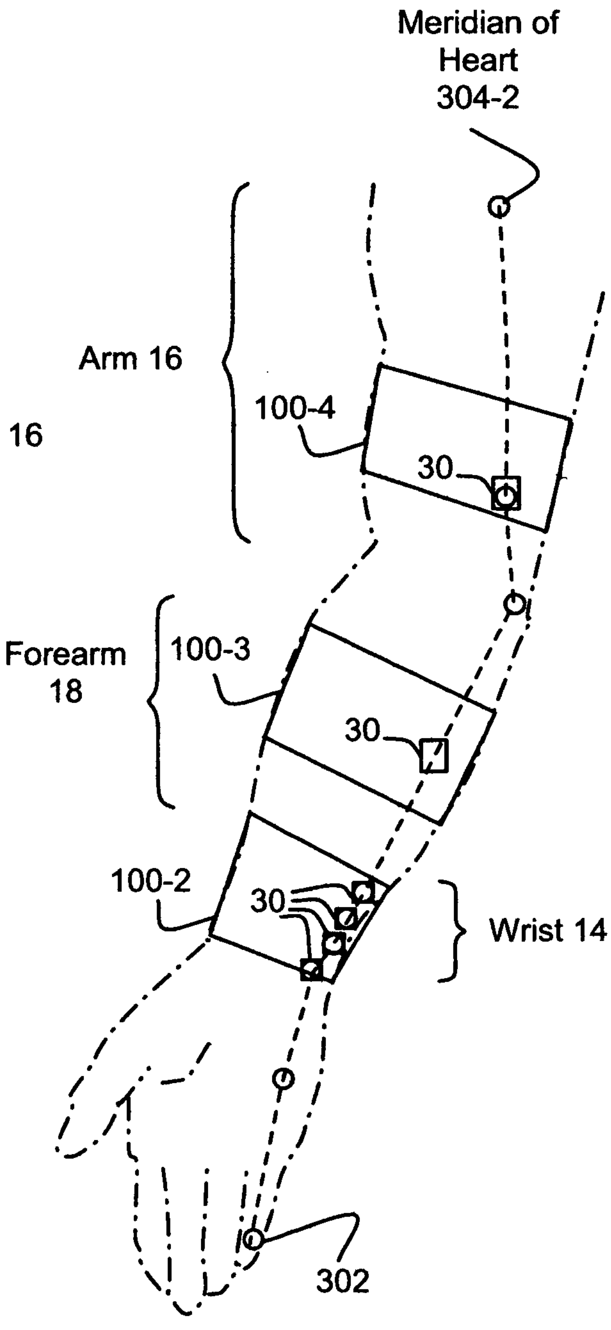
Figure 3A:
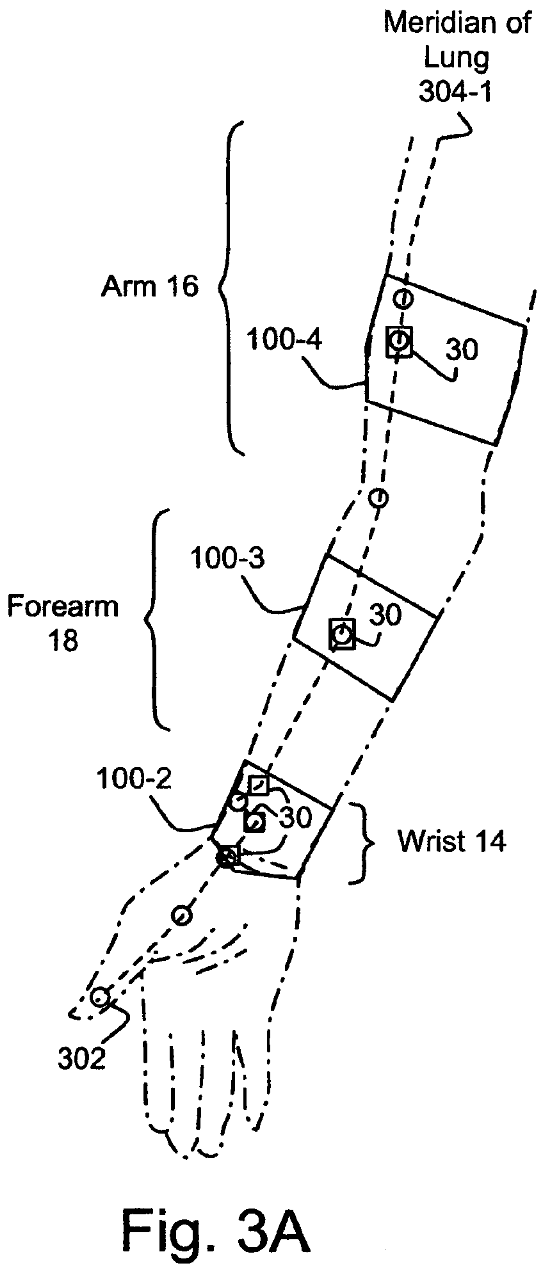
Figure 3B:
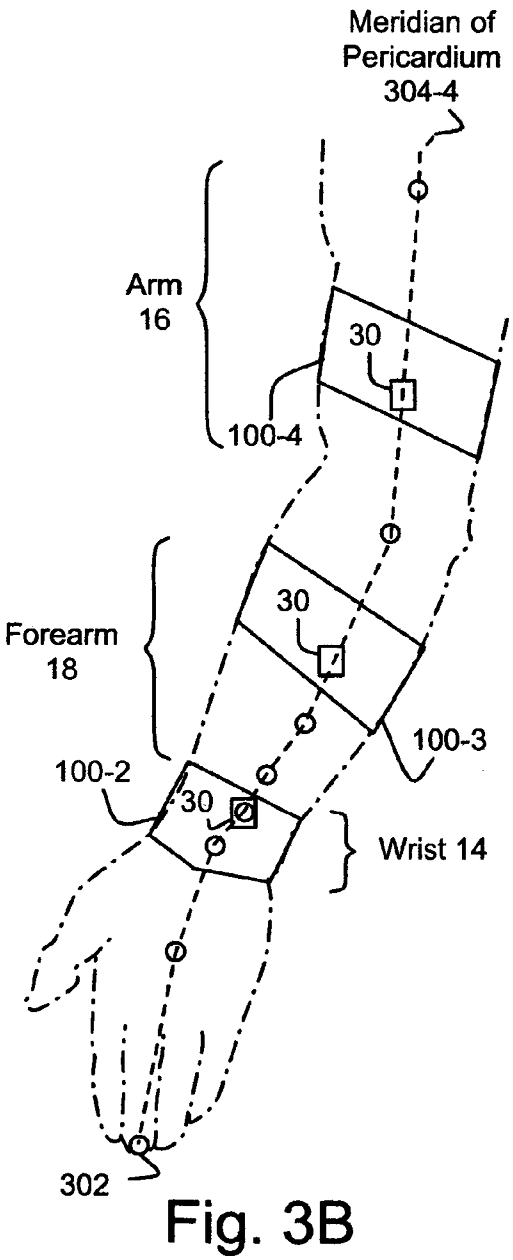

The wearable infrastructure 100, which may preferably stimulate the meridian of the lung 304-1, as shown in FIG. 3A. The wrist harness may further preferably stimulate the meridian of the heart 304-2, as shown in FIG. 2B. It may further preferably stimulate the meridian of the pericardium 304-4 as in FIG. 3B, and/or the meridian of the triple warmer 304-3 as in FIG. 2A. The meridian of the triple warmer is also known as the triple burner meridian.

Returning to the invention's operation, which includes the following steps. Keeping at least one transponder 30 near at least one biologically active zone 300 of a user 10 wearing the transponder. Using the transponder to provide the symbol sequence 200 to the biologically active zone of the user. Keeping the transponder near the biologically active zone may further include keeping the transponder touching 34 the biologically active zone at least some of the time, and in certain embodiments, all the time the invention is operating.

Using the transponder 30 may include using it to acoustically provide 36 the symbol sequence 200 to more than one biologically active zone 300.

Using the transponder 30 may include using it to acoustically provide 36 the symbol sequence 200 within a given time period. The time period may be repeated and/or vary over time.

The wearable infrastructure 100 may further provide a mechanism by which the music/multimedia player 20 may be held. This may be as a space to clip the music/multimedia play.

Keeping at least one transponder near at least one biologically active zone may include keeping more than one of the transponders near more than one of the biologically active zones, as shown in FIGS. 4B and 5A. While in this application, there is a preference for the carrier medium to be acoustic, in certain embodiments, there may be more than one preferred carrier medium. The biologically active zones may or may not all be from the same medical system. By way of example, acupuncture point and trigger points may be used for the biologically active zones.

The apparatus of the wearable infrastructure 100 may be seen in light of its operations, as in FIGS. 1A, 1B, 7B and 7C. The wearable infrastructure may include at least one means for keeping 110 a transponder 30 near 38 a biologically active zone 300, preferably as found on an appendage 12 of a user 10. The wearable infrastructure also includes a means for coupling 120 the wearable infrastructure about an appendage 12 of the user 10. The appendage may be a wrist 14, an arm 16, or a forearm 18 of the user. The wearable infrastructure may further include a means for muffling 130 the transponder from the ears of the user Alternatively, apparatus of the wearable infrastructure 100 may be seen in light of components, as in FIGS. 1C, 1D, 7D, 7E, and 9C to 12B. The wearable infrastructure may include a harness 150 containing a site 170 for a transponder 30, which may preferably be a headphone 32. The harness may include a backing 172, which may preferably muffle the transponder. The harness may further include a harness coupling surface 174, whether or not it includes the backing.

The wearable infrastructure 100 also includes a band 160 coupling said wearable infrastructure about the appendage 12 of said user 10. The band preferably includes a first binding surface 164 and a second binding surface 166, by which the band is coupled about the appendage. The first and second binding surfaces may form any two component latch, including but not limited to mating hook and loop surfaces, mechanical latches, and belt buckle arrangements. The wearable infrastructure 100 may be made by coupling the band 160 to at least one harness 150.

The wearable infrastructure 100 may include a second harness 150-2, as shown in FIGS. 11A to 12B. The second harness 150-2 provides a second site 170-2 for a second transponder 30-2, often a second headphone 32-2. The harness 150 and the second harness may share a backing 172, or the second harness may have a second backing 172-2. The harness and the second harness may be bonded to the band 160, as in FIG. 11A. The harness and the second harness may share a harness coupling surface, of the second harness may have a second harness coupling surface 174-2. The harness coupling surface and when present, the second harness coupling surface, are positioned over the harness binding zone 162, and pressed down to create the wearable infrastructure configured for a specific user 10 and their specific appendage 12.

The wearable infrastructure 100 may include keeping the second headphone 32-2 near 38, possibly touching 34, the second biologically active zone 300-2, as shown in FIGS. 4B and 5A. Additionally, the wearable infrastructure may keep more than two headphones near additional biologically active zone. By way of example, FIG. 5A shows the wearable infrastructure keeping a third headphone 32-3 near, possibly touching, a third biologically active zone 300-3. The wearable infrastructure is also keeping a fourth headphone 32-4 near, possibly touching, a fourth biologically active zone 300-4.

Figure 6A:
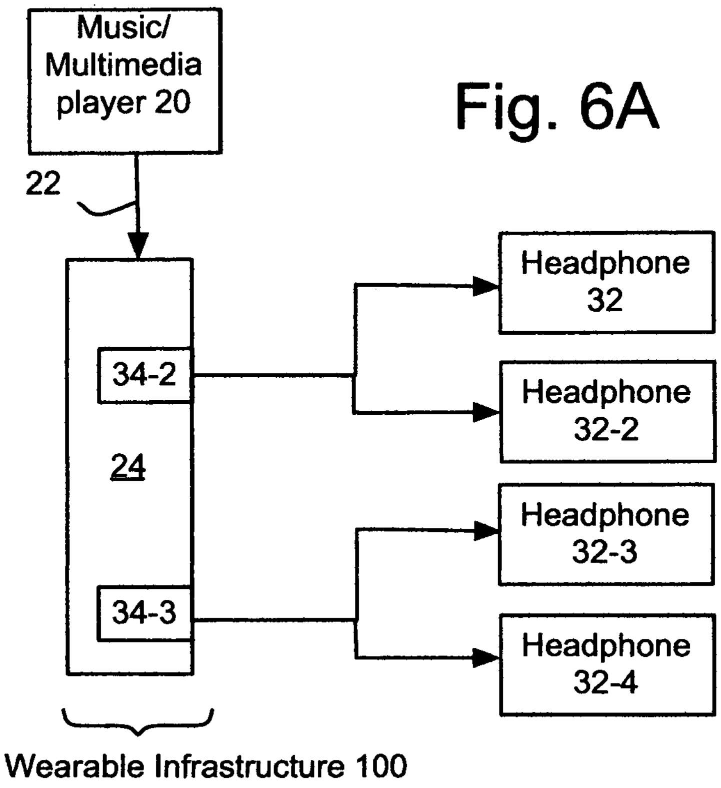

FIG. 6A shows a basic schematic of the use of a distribution device 24 in the wearable infrastructure 100. The music/multimedia player 20 delivers 22 the symbol sequence to the distribution device, which may preferably provide a second headphone jack 34-2 and a third headphone jack 34-3, to distribute the symbol sequence to the headphone 32, the second headphone 32-2, the third headphone 32-3, and the fourth headphone 32-4.

Figure 6B:
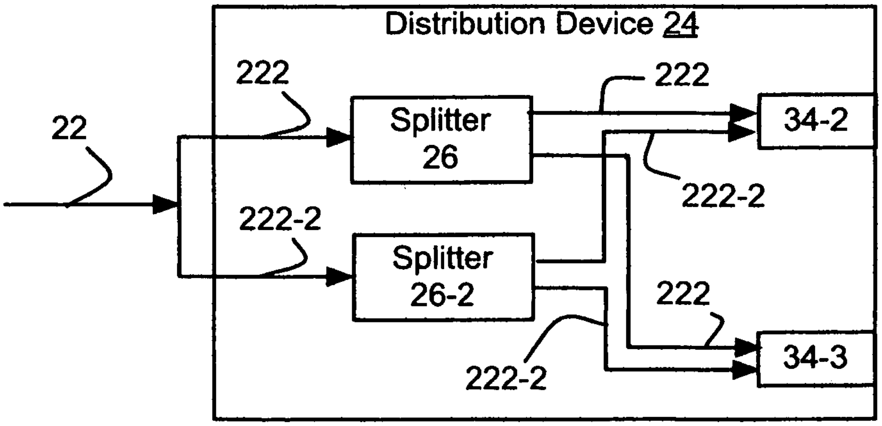
Figure 7A:
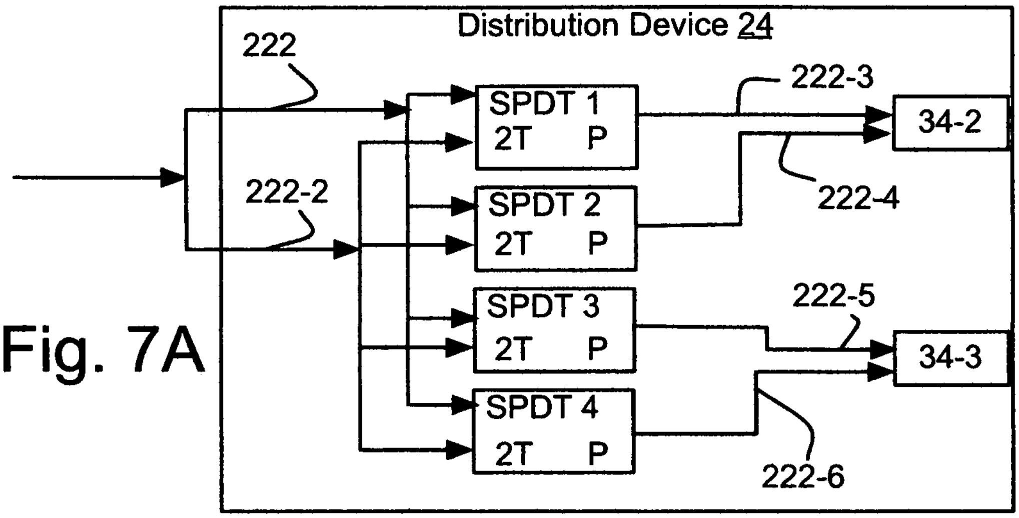
Figure 7B:
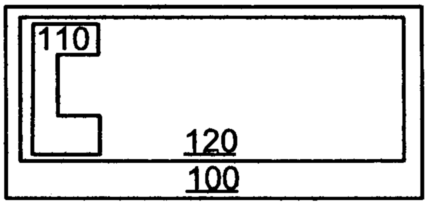
FIGS. 7B to 7E show details of the wearable infrastructure of FIGS. 1A to 1D.
Figure 7C:
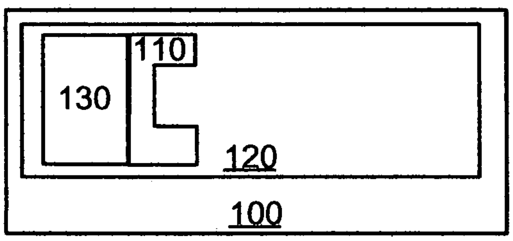
Figure 7D:
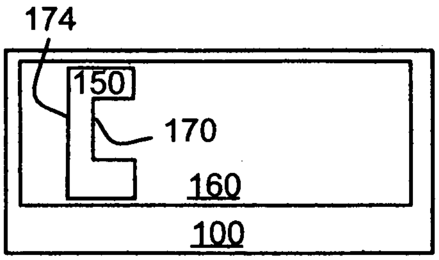
Figure 7E:
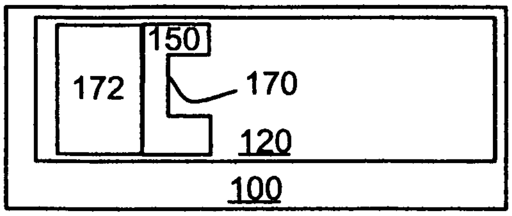

FIGS. 6B and 7A show two examples of the distribution device 24 used in the wearable infrastructure 100 of FIG. 6A. Often the delivery of the symbol sequence 200 involves a wire line physical transport 220, though the similar circuitry can support the wireless physical transport 230.

In FIG. 6B, a first audio channel 222 and a second audio channel 222-2 are used to deliver the symbol sequence as modulated signals. The first audio channel is presented to a first splitter 26, which drives the first audio channel to both the first headphone jack 34 and the second headphone jack 34-2. The second audio channel is presented to a second splitter 26-2, which drives the second audio channel to both the first headphone jack 34 and the second headphone jack 34-2. In some cases, these splitters may be embodied as a direct connect of all the ports of the device.

In FIG. 7A, the first audio channel 222 and the second audio channel 222-2 are each presented to the throw terminals of a collection of Single Pole Double Throw (SPDT) switches. The pole terminals of pairs of these SPDT switches are then presented to a headphone jack for each of the two headphones. More specifically, SPDT 1 and SPDT 2 present their poles to the second headphone jack 34-2. SPDT-3 and SPDT-4 present their poles to the third headphone jack 34-3.

Figure 9C:
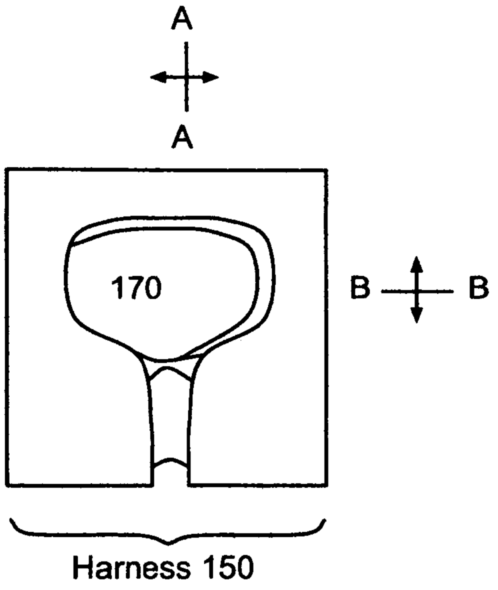
FIGS. 9C to 10F shows some details of the harness of preceding Figures.
Figure 9D:
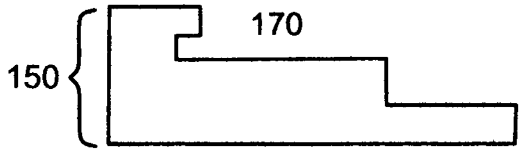
Figure 9E:
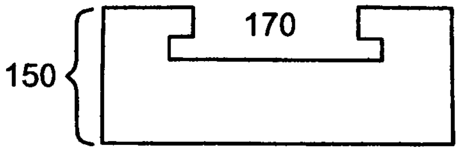
Figure 9F:
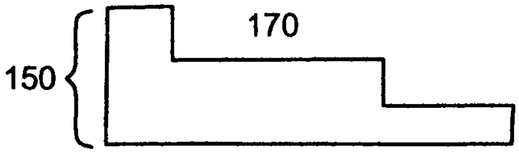
Figure 9G:
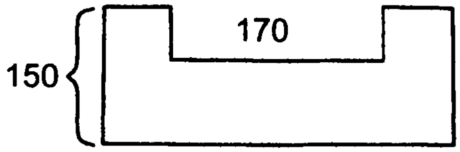
Figure 10A:
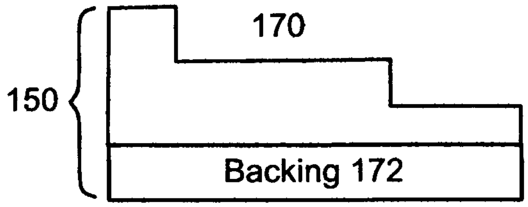
Figure 10B:
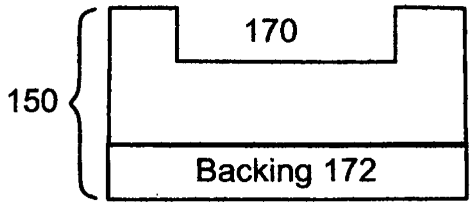
Figure 10C:
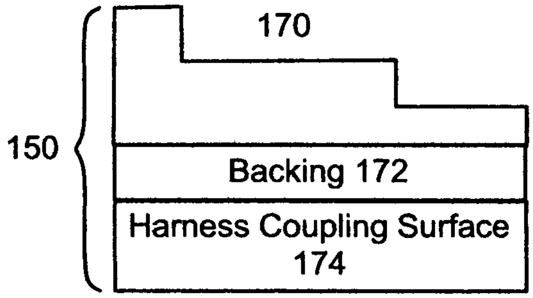
Figure 10D:
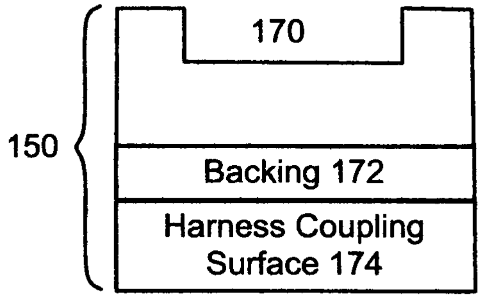
Figure 10E:
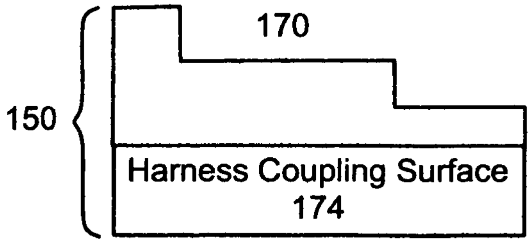
Figure 10F:
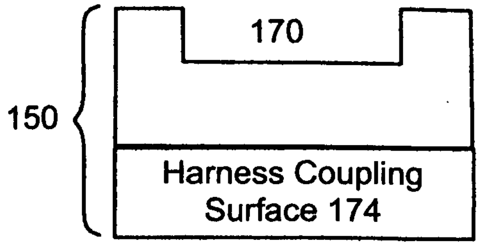
Figure 11A:
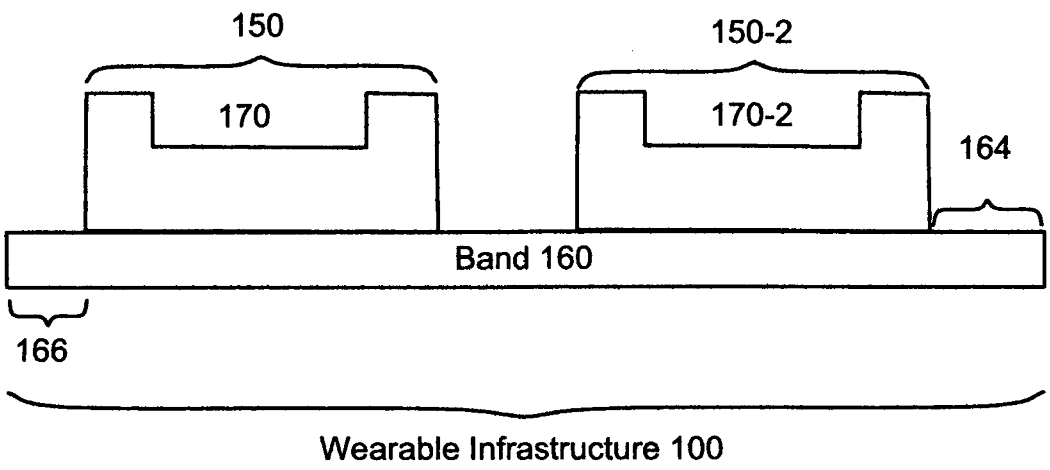
FIGS. 11A to 12B show some mechanical details of the wearable infrastructure of the preceding Figures.
Figure 11B:
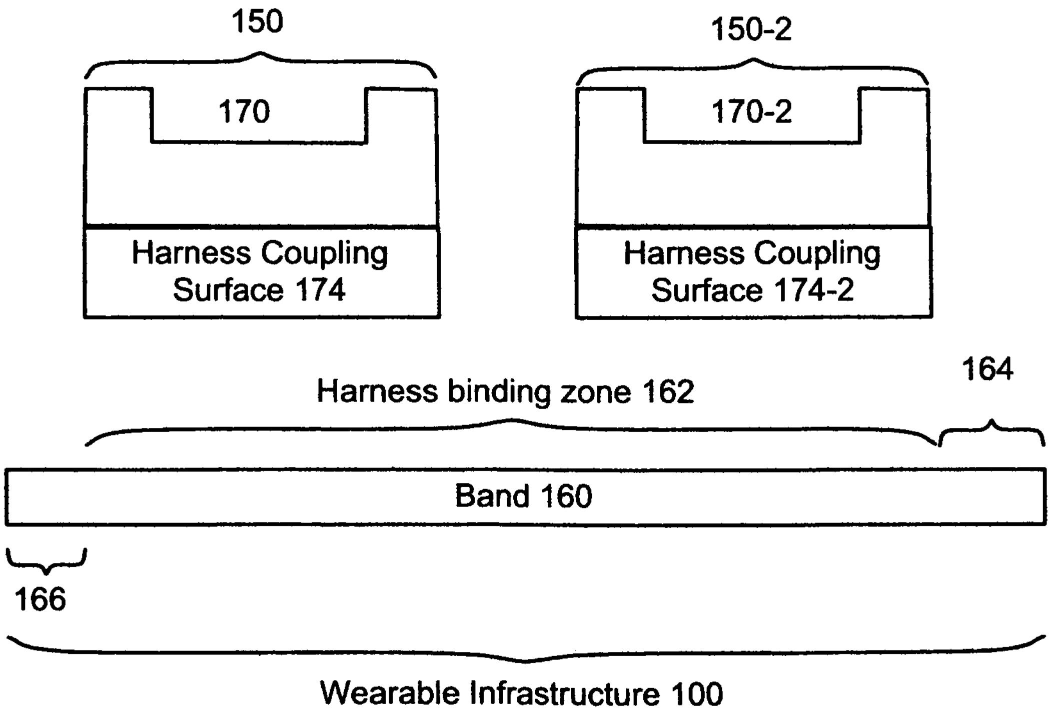
Figure 12A:
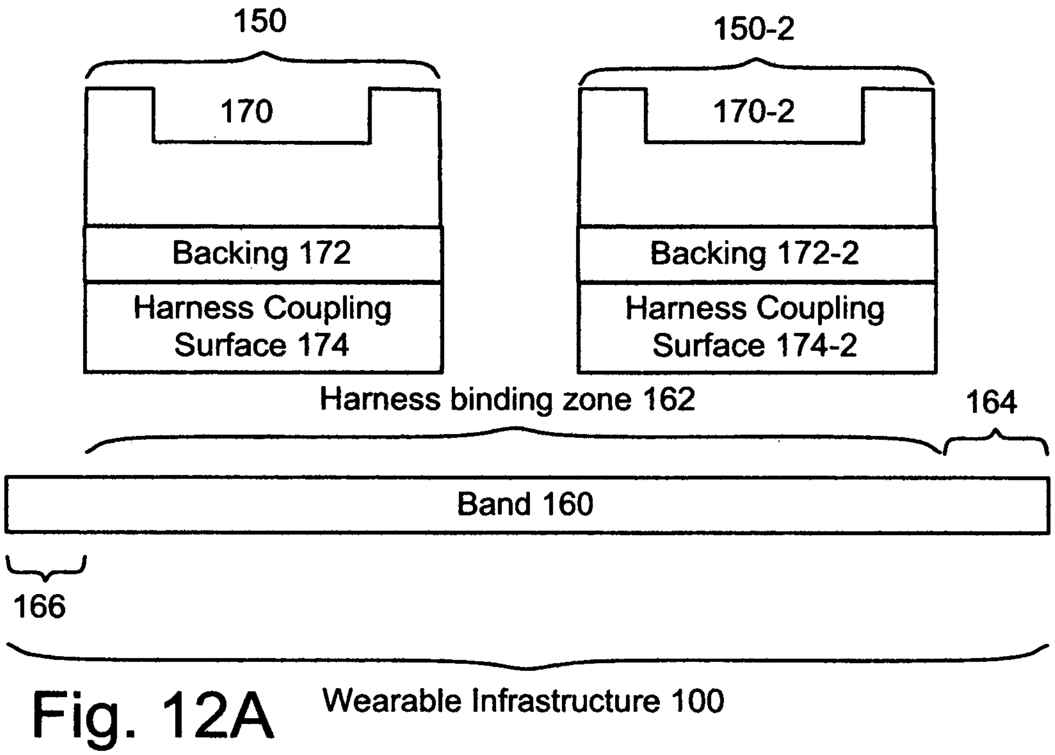
FIG. 12C shows a diagram of Song Park's meta-alphabet as disclosed on and incorporated herein from pages 12 and 13 of the provisional application No. 60/605,278.
Figure 12B:
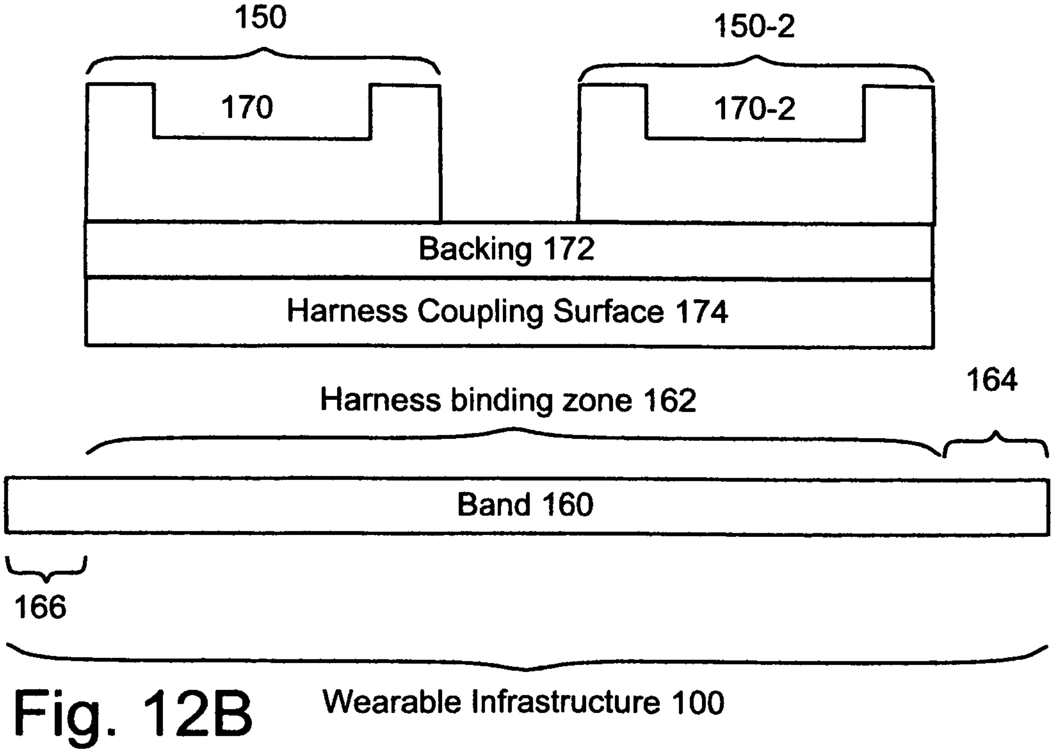

Returning to the apparatus of the harness 150, FIG. 9C shows a view from the appendage 12, showing the site 170 for the transponder 30. Two example embodiments of the harness will be discussed. FIGS. 9D and 9F show the two embodiments for the A-A perspective of FIG. 9C. FIGS. 9E and 9G show them from the B-B perspective. FIGS. 9D and 9E show the site with a lip by which to hold the transponder. Particularly when the transponder is a typical headphone 32 of a contemporary music/multimedia player 20, this can be useful. FIGS. 9F and 9G show the site without a lip by which to hold the transponder. If the headphone and/or transponder is to be permanently mounted, perhaps by gluing, this can be useful.

The preceding embodiments provide examples of the invention and are not meant to constrain the scope of the following claims.

What is claimed is:

1. A method, comprising:

acoustically providing at least one symbol sequence of at least two symbols formed of spoken letters in a meta-alphabet including spoken letters of at least one vowel and at least one consonant to at least one biologically active zone on a user from a wrist through an arm of said user, further comprising the steps of:

keeping at least one transponder near at least one of said biologically active zones on said user; wherein said user is a human being;

said transponder receiving said symbol sequence from a music/multimedia player to; and said transponder providing said symbol sequence to said at least one biologically active zone through an acoustic carrier medium as sound to said user;

wherein said at least one biologically active zone is at least one member of a group, consisting of:

at least one point of a meridian, at least one reflexology correspondence point, at least one pressure point, at least one region named and used in Tibetan medicine, at least one point named and used in said Tibetan medicine, at least one respiratory system point, at least one respiratory system region, at least one muscular system point, at least one muscular system region, at least one arterial system point, at least one arterial system region, at least one fascial system point, at least one fascial system region, at least one nervous system point, and at least one nervous system region.

2. The method of claim 1, wherein each of said symbols included in said symbol sequence belong to the spoken letters of said meta-alphabet.

3. The method of claim 1, further comprising a step of:

providing a wearable infrastructure;

wherein said wearable infrastructure, comprises:

said transponder providing said symbol sequence to said at least one biologically active zone through an acoustic carrier medium as sound to said user;

means for keeping said at least one transponder near said at least one biologically active zone on said user when wearing said wearable infrastructure; and means for coupling said wearable infrastructure about an appendage, whereby said appendage is a member of a group consisting of: at least one arm of said user, at least one wrist of said user, and at least one forearm of said user.

4. The method of claim 3, wherein the means for keeping, further comprises at least one member of the group consisting of:

means for keeping a first transponder near a first biologically active zone;

means for keeping a second transponder near a second biologically active zone;

means for keeping a third transponder near a third biologically active zone; and means for keeping a fourth transponder near a fourth biologically active zone.

5. The method of claim 4, wherein the means for keeping, further comprises at least one member of the group consisting of:

means for keeping said first transponder touching said first biologically active zone;

means for keeping said second transponder touching said second biologically active zone;

means for keeping said third transponder touching said third biologically active zone; and means for keeping said fourth transponder touching said fourth biologically active zone.

6. The method of claim 4, wherein said first biologically active zone is a meridian of a lung of said user;

wherein said second biologically active zone is a meridian of a heart of said user;

wherein said third biologically active zone is a meridian of a pericardium of said user; and wherein said fourth biologically active zone is a meridian of a triple warmer of said user.

7. The method of claim 3, wherein the means for keeping, includes:

means for muffling said sound from said transponder from ears of said user.

8. The method of claim 1, further comprising a step of:

providing a wearable infrastructure;

wherein said wearable infrastructure, comprises:

a harness keeping said at least one transponder near said at least one biologically active zone on said user when wearing said wearable infrastructure; and a band adapted to couple said wearable infrastructure about an appendage of said user, whereby said appendage includes at least one member of a group consisting of: at least one arm of said user, at least one wrist of said user, and at least one forearm of said user.

9. The method of claim 8, wherein said harness is configured to:

keep a first transponder near a first biologically active zone on said user;

keep a second transponder near a second biologically active zone on said user;

keep a third transponder near a third biologically active zone on said user; and/or keep a fourth transponder near a fourth biologically active zone on said user.

10. The method of claim 9, wherein said harness is further configured to:

keep said first transponder touching said first biologically active zone on said user;

keep said second transponder touching said second biologically active zone on said user;

keep said third transponder touching said third biologically active zone on said user; and/or keep said fourth transponder touching said fourth biologically active zone on said user.

11. The method of claim 10, wherein said first biologically active zone is a meridian of a lung of said user;

wherein said second biologically active zone is a meridian of a heart of said user;

wherein said third biologically active zone is a meridian of a pericardium of said user; and wherein said fourth biologically active zone is a meridian of a triple warmer of said user.

12. The method of claim 8, wherein said harness, comprises: an adjustable site for said transponder configured to place said transponder near one of said biologically active zones on said user.

13. The method of claim 12, wherein said harness, further comprises: a backing to said site to acoustically dampen said symbol sequence being heard by at least one ear of said user.

14. The method of claim 8, wherein said transponder, includes: at least one headphone.

15. The method of claim 14, wherein said transponder receives said symbol sequence delivered by said music/multimedia player through at least one member of a group, consisting of:

a wire line physical transport to a headphone jack included in said music/multimedia player; and a wireless physical transport to said music/multimedia player using a wireless communications protocol.

16. The method of claim 15, wherein said wire line physical transport couples a second of said headphones to said headphone jack.

17. The method of claim 1, further comprising the step of:

storing a symbol coding sequence in a music/multimedia player and/or a memory as a program system configured to direct the computer to deliver said symbol sequence to said at least one transponder to provide said symbol sequence to said biologically active zone through said acoustic carrier medium as sound.

18. The method of claim 17, wherein said program system includes program steps coded in an intermediate language.

19. The method of claim 18, wherein said intermediate language is included in a version of a Motion Picture Exchange Group (MPEG) language.

20. The method of claim 19, wherein said MPEG language includes at least one member of the group, consisting of: a MPEG 1 language, a MPEG 2 language, a MPEG 3 language, and a MPEG 4 language.

21. The method of claim 18, wherein said intermediate language is compatible with a version of Windows Media File Format.

* * * * *